US012008854B2

(12) United States Patent
Sauer et al.

(10) Patent No.: US 12,008,854 B2
(45) Date of Patent: Jun. 11, 2024

(54) SYSTEMS AND METHODS FOR PROVIDING IDENTITY INFORMATION

(71) Applicants: Joseph Sauer, Lombard, IL (US); Alan Sorrill, Wheaton, IL (US); Hokuto Nishioka, Chicago, IL (US); Vijay Putherickal, Des Plaines, IL (US); Christopher Deeble, Fair Oaks, CA (US); Nicholas Green, Riverside, IL (US)

(72) Inventors: Joseph Sauer, Lombard, IL (US); Alan Sorrill, Wheaton, IL (US); Hokuto Nishioka, Chicago, IL (US); Vijay Putherickal, Des Plaines, IL (US); Christopher Deeble, Fair Oaks, CA (US); Nicholas Green, Riverside, IL (US)

( * ) Notice: Subject to any disclaimer, the term of this patent is extended or adjusted under 35 U.S.C. 154(b) by 708 days.

(21) Appl. No.: 17/058,751

(22) PCT Filed: May 28, 2019

(86) PCT No.: PCT/US2019/034172
§ 371 (c)(1),
(2) Date: Nov. 25, 2020

(87) PCT Pub. No.: WO2019/227097
PCT Pub. Date: Nov. 28, 2019

(65) Prior Publication Data
US 2021/0134098 A1 May 6, 2021

Related U.S. Application Data

(60) Provisional application No. 62/676,637, filed on May 25, 2018.

(51) Int. Cl.
*G08B 1/08* (2006.01)
*G07C 9/28* (2020.01)
*G16H 40/20* (2018.01)

(52) U.S. Cl.
CPC ............... *G07C 9/28* (2020.01); *G16H 40/20* (2018.01)

(58) Field of Classification Search
CPC . G07C 9/28; G07C 1/10; G16H 40/20; G08B 21/02; G08B 13/19613; G08B 13/2462; G08B 25/08
(Continued)

(56) References Cited

U.S. PATENT DOCUMENTS 11,355,232 B2 * 6/2022 Greiner .................. G16H 40/20
2002/0086663 A1 * 7/2002 Tang ...................... G06Q 30/02
455/414.1
(Continued)

FOREIGN PATENT DOCUMENTS

WO 2015/157575 10/2015

OTHER PUBLICATIONS

Teixeira, et al., A Survey of Human-Sensing: Methods for Detecting Presence, Count, Location, Track and Identity, Enalab Technical Report Sep. 2010, vol. 1, No. 1, Sep. 2010.
(Continued)

*Primary Examiner* — Tai T Nguyen
(74) *Attorney, Agent, or Firm* — Smith Keane LLP

(57) ABSTRACT

Systems for providing and tracking information, including location and credentials, of a person and providing this information to a user on a display. The system provides multiple views on the display including a room view to indicate who is in a specified room or other location, a team view to indicate a person's position in an overall service
(Continued)

team, and a timeline view to indicate the times and durations of service events involving one or more persons.

23 Claims, 10 Drawing Sheets

(58) Field of Classification Search
USPC .................................................. 340/539.13
See application file for complete search history.

(56) References Cited

U.S. PATENT DOCUMENTS

| | | |
|---|---|---|
| 2006/0261952 A1 | 11/2006 | Kavounas et al. |
| 2007/0162304 A1 | 7/2007 | Rodgers |
| 2015/0371522 A1* | 12/2015 | Mravyan ................. H04W 4/80 340/573.1 |
| 2016/0180033 A1* | 6/2016 | Rosenberg ........... G06Q 10/087 705/2 |
| 2017/0287316 A1 | 10/2017 | Wildman et al. |

OTHER PUBLICATIONS

International Search Report and Written Opinion of the ISA, dated Aug. 8, 2019, from related PCT Application Serial No. PCT/US2019/034172, Filed May 28, 2019, 11 pages.

* cited by examiner

SYSTEMS AND METHODS FOR PROVIDING IDENTITY INFORMATION

BACKGROUND

Comprehensive treatment of patients in hospitals and other healthcare facilities is generally performed by a number of service providers, including doctors, physician assistants, nurses, and others, all part of a broader treatment team. Although it has been common prior practice of staff in hospitals to wear identification badges, patients and their loved ones often find identification badges difficult to read because of low or inadequate lighting, poor eyesight, and/or staff movement (e.g., staff are often in motion when one attempts to read an ID badge).

Moreover, in certain care environments, it is common for staff to wear hospital scrubs. Sometimes, hospital scrubs are the same make, color, and style for all members of a treatment team. Additionally, at times the medical staff are wearing surgical face coverings, head coverings, and shoe coverings while interacting with patients and their families which makes staff identification even more challenging. Accordingly, due to substantial uniformity in appearance of, and relative infrequent and short durations of interactions with, staff members (e.g., hospital staff members), staff member identity can be difficult to discern.

Further, even when staff are positively identified, it is often difficult for a patient to ascertain the role of a given staff member within the treatment team and the care that member has provided in the past, is providing, or will provide over time (prospectively). For example, it can be difficult to distinguish ranks of staff members, such as between a resident, senior resident, fellow, or attending physician—or to determine how these various staff members from different departments interface with one another or at what stage within the chronological order of care in a given treatment scenario they have provided, or will provide, care.

Additionally, there are times when other professionals (e.g., technicians, nursing assistants, nurses, physician assistants, and vendor representatives) will consult with the patient or render ancillary support, many of whom may wear nearly or exactly the same scrubs or uniforms as physicians and other staff.

Moreover, there are often important distinctions between members of a given staff type. For example, nurses may be distinguished by having a plurality of training levels that may be relevant to the provision of skilled care (i.e., Nurse R.N., Nurse B.S., Nurse M.S., or Nurse Ph.D.).

Sadly, patients and their loved ones all too often accept a significant degree of confusion in a hospital or other care or service setting and accept a limited knowledge of the identities of the various members of the service team and how they fit into the provision of services, requiring a level of trust that may be nervous at best. This limited knowledge often produces tremendous frustration when interacting with staff because of the inability to positively identify staff by name, title, or department and their role in a treatment team.

On the other hand, from the staff perspective, it is often difficult to identify patients and their loved ones because staff care for so many individuals over time. Therefore, the art of patient care is in need of a system that better tracks and identifies persons providing treatment, receiving treatment, and those ancillary to the treatment.

SUMMARY OF THE INVENTION

The instant invention relates generally to the field of identifying persons providing, receiving, and ancillary to the provision of a service. More specifically the present invention is directed to identifying certain persons and associating the identified persons with their respective work histories, including location, and their respective position(s) within the provision of the service and/or within the service team.

According to an embodiment of a system according to the present invention, a first code detector is capable of detecting a first code and a second code in a physical space (e.g., doorway, hallway, room, portion of a room). The first code detector is communicatively coupled to a communication network (e.g., wired and/or wireless, LAN, WAN, internet, etc.) and capable of transmitting code detections over the network. A data manager receives and is capable of monitoring and analyzing the code detections sent by the code detector over the communication network. An informational database (relational or flat) is capable of storing information from and providing information to the data manager. A display device is located in a building housing the physical space. The display device receives information from the data manager and includes a timeline view that graphically displays a time differential that occurs between a first time at which the first code is detected in the physical space and a second time at which the first code is detected in the physical space, the time differential being the difference of a first time at which the second code is detected in the physical space and a second time at which the second code is detected in the physical space. Basically, a preferred time differential is an amount of time that indicates at least two codes have been detected as passing through a particular space and one of the codes has left that space.

According to an aspect of an embodiment according to the present invention, the first code is logically associated with a representation (e.g., name or photo) of a first object in the informational database, and the first code is also physically associated with (e.g., attached or coupled to) the first object. The first object may be a human being, such as a hospital patient.

According to another aspect of an embodiment according to the present invention, the second code is logically associated with a representation (e.g., name or photo) of a second object in the informational database, the second code is physically associated with the second object. The second object may be a human being, such as a hospital caregiver.

According to still another aspect of an embodiment of a system according to the present invention, code detections include information sent to a uniform resource locator (URL) over the communication network. The data manager may include or otherwise have access to a software script hosted at the uniform resource locator, the script being executed as a result of receipt of one of the code detections.

According to yet another aspect of an embodiment of a system according to the present invention, such system may further include a second code detector capable of detecting the first code and the second code in the physical space, the second code detector being communicatively coupled to the communication network and capable of transmitting code detections over the network. Each code detector preferably includes at least one antenna for wirelessly detecting codes (e.g. RFID tags) in a given space. Each antenna has a radiation pattern and preferably all antennas that are used in detecting codes in the physical space are arranged such that all radiation patterns (e.g. main lobes of radiation) overlap throughout a majority of the physical space.

According to a further aspect of an embodiment of a system according to the present invention, each code detection sent by the code detector (e.g., waypoint) comprises information related to at least one of the first code, the second code, the physical space, a building (e.g., hospital) containing the physical space, and time of day. The physical space may be less than an entire room (e.g., defined by walls) and the room preferably contains at least one bed, such as a patient bed.

According to a still further aspect of an embodiment of a system according to the present invention, the display device further includes a room view that graphically displays information associated with the second code, the graphical display being accessible between the first time at which the second code is detected in the physical space and a second time at which the second code is detected in the physical space.

According to yet a further aspect of an embodiment of a system according to the present invention, the first code detector is capable of detecting a third code in the physical space, the display device further comprising a team view that graphically displays information associated with the second code and information associated with the third code, the graphical display presenting the second code information related to the third code information in a hierarchical fashion.

According to an aspect of an embodiment of a method according to the present invention includes the steps of detecting a first entry of a first code in a physical space and detecting a first entry of a second code in the physical space, which may occur after detecting the first entry of the first code. After detecting the first entry of the second code, a second entry of the second code into the physical space is detected. At least one set, and preferably one set for each of the code entries (e.g., preferably first, second, and third), of parameters are transmitted to a database manager wherein each set of parameters include at least two of the following: information related to a building housing the physical space, information related to the physical space, code information, and a timestamp.

According to another aspect of an embodiment of a method according to the present invention, prior to detecting the first entry, the first code may have been physically associated with a first object and the second code physically associated with a second object. The first object may be a human being, such as a hospital patient. The second object may be a human being, such as a hospital caregiver.

According to still another aspect of an embodiment of a method according to the present invention, the physical space includes at least a portion of a doorway defined above a floor, such as from a height of about 50 cm from the floor to a height of about 150 cm, and more specifically from a height of about 80 cm to a height of about 150 cm. Rather than be in a doorway, the physical space (including at the stated dimensions) may be defined as a portion of a room, the room including at least two beds.

According to an aspect of another embodiment of a method according to the present invention, it includes receiving a first set of parameters relating to a first code associated with a first object. After receiving the first set of parameters, a second set of parameters relating to a second code associated with a second object is received. After receiving the second set of parameters, and after receiving a request from a display device (or without a request from the display device), transmitting to the display device information associated with the second code (such as a photograph of the second object or a characteristic of the second object) and a time differential.

DETAILED DESCRIPTION

Although the disclosure hereof enables those skilled in the art to practice the invention, the embodiments described merely exemplify the invention which may be embodied in other ways. While the preferred embodiment has been described, the details may be changed without departing from the invention. It should be noted that like part numbers represent like parts among the various embodiments.

Figure 1:
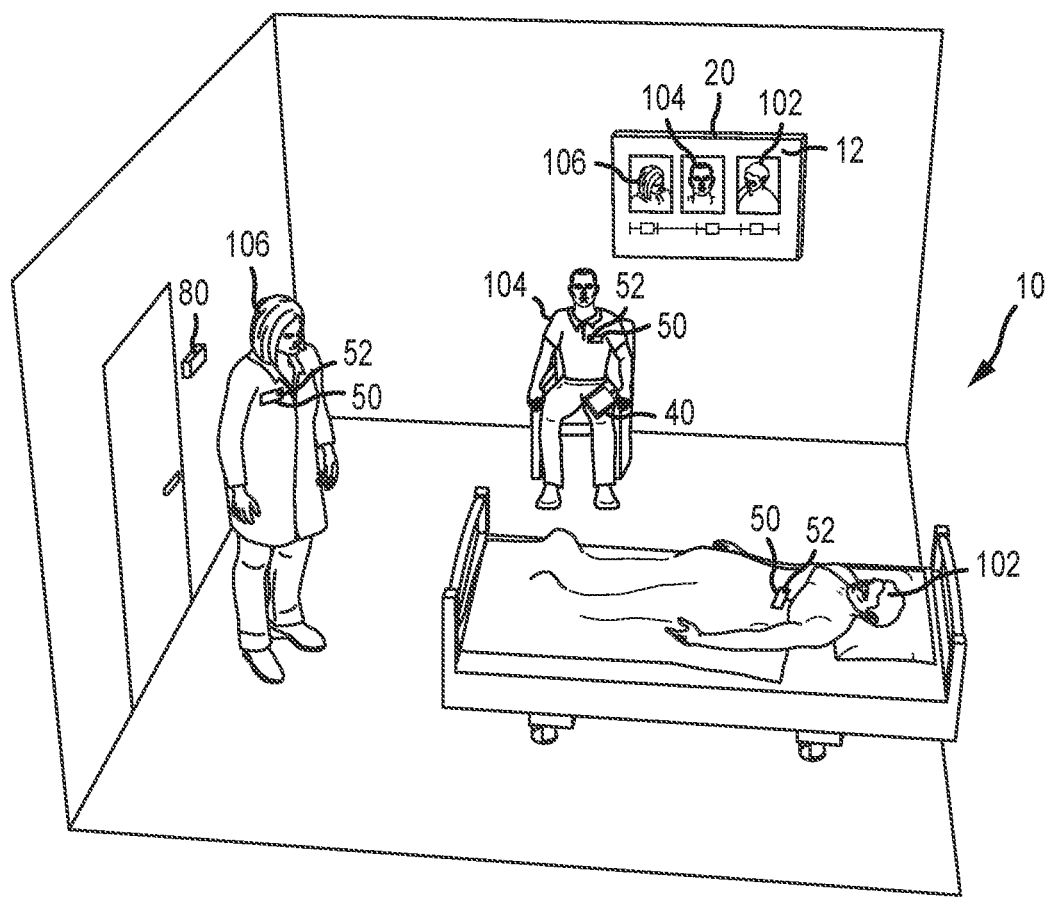
FIG. 1 is a perspective view of an embodiment of the present invention.

To simplify the disclosure of the present invention, it will be described as it may be applied in the medical field, but it should be understood that broader applications are contemplated. To further the understanding of the present invention, the term "user" may include a patient 102 (FIG. 1), a patient's family 104 (FIG. 1), friend, a hospital administrator, an employee 106 (FIG. 1), insurance adjustor, or other individual. The term "employee" is any individual allowed to work in a given location (e.g., in a hospital setting, "employee" includes physicians, nurses, technicians, physician assistants, medical students, nursing students, trainees, administrative staff, custodial staff, vendor representatives, pharmacists, social workers, consultants, and other individuals permitted to render service or to appear in any capacity to study or to render consultation, service, or advice). "Rendering care" or the like is synonymous with consultation, surgical intervention, pharmacological intervention, radioisotope intervention, phototherapy, diagnostic intervention of any type (e.g., x-ray, CT scan), specimen collection (e.g., blood, urine, semen, cerebrospinal fluid (CSF), tissue biopsy), or any medical care. "Rendering care" may also apply to non-medical scenarios in which an employee provides any service. The term "location" means an actual physical location, relative location (e.g., with respect to a user), or the presence of an individual with respect to a user.

The present invention is directed to a system 10 for identifying and tracking the location of persons. The system 10 comprises a display 12 for providing information to a user. For example, the information preferably includes the name, title, position within a treatment team, location, and/or treatment role over time including past, present, and future, collectively "employee information"; information about a patient including name, medical history, treatment plan, medications, location etc., collectively "patient information"; and information regarding vendors (e.g., name, company, location), patient's family members (e.g., names, relationship to patient, location, permissibility), non-family member visitors (e.g., names, relationship to patient, location, permissibility), collectively "ancillary person information." It should be noted that the information included in these categories is customizable and, in certain circumstances, some information may be preferably not included (e.g., disclosure of patient medical history and/or test results could run afoul of certain compliance regulations and/or privacy concerns).

Figure 2:
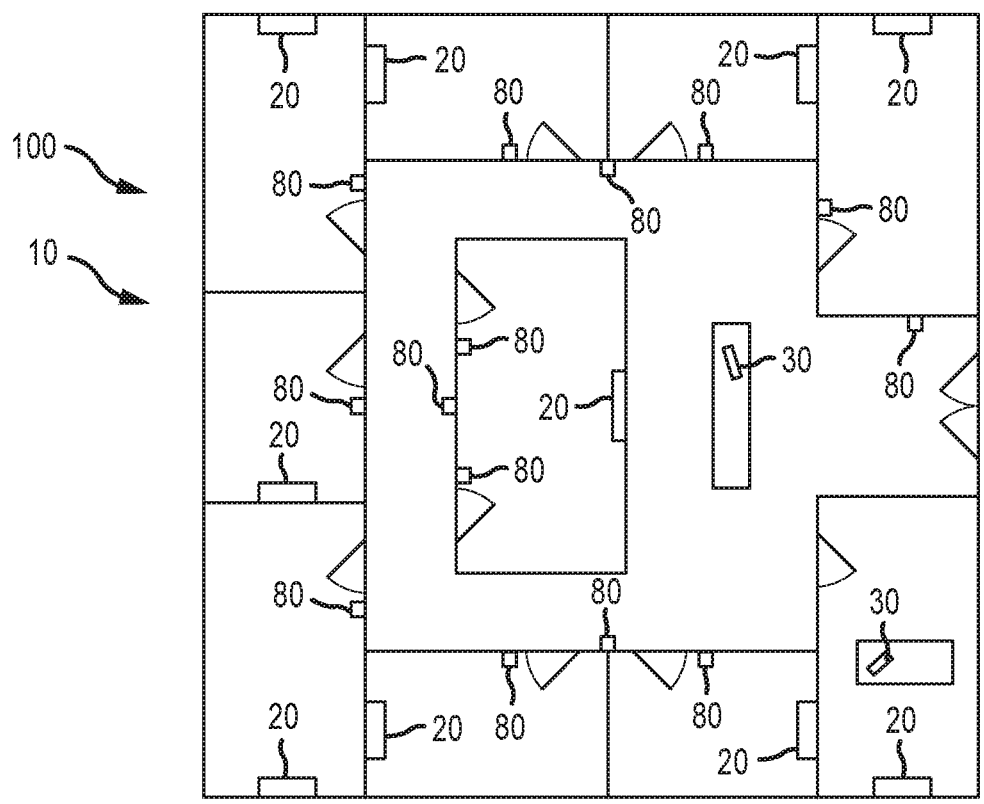
FIG. 2 is a top floorplan view of a facility in which the present invention is provided.

The display 12 may be integral to a device now known or later developed which is capable of displaying information to the user, including but not limited to, a television monitor 20 (FIG. 1), a computer monitor 30 (FIG. 2), a tablet 40 (FIG. 1), a mobile phone, a watch, virtual reality goggles, augmented reality goggles. The display 12 may be generated by a device, such as an image projector (including backlit, forward-throw projector), heads up display, or holographic display. It is also contemplated that auditory sounds and/or tactile feedback such as vibration may also be provided to relay information to a user.

Preferably, the system 10 further comprises identification badges 50, or the like, which incorporate a communication mechanism 52 for relaying the respective aforementioned information of an employee, patient, and/or ancillary person from the badge 50 to be used in the system 10. Any communication mechanism now known or later developed capable of transmitting information as described herein may be used. Non-limiting examples of a communication mechanism include a magnetic stripe interface, contact-type smart card interface, and/or communication technology such as radio-frequency identification (RFID), near-field communication (NFC), Wi-Fi®, and/or BLUETOOTH® telecommunication. Staff may also be identified through the use of biometric recognition techniques such as facial recognition, vascular recognition (including retinal scans), and/or fingerprint recognition.

The employee information, patient information, and ancillary person information may be stored in or on a storage medium (e.g., magnetic stipe (low or high coercivity), RFID, or NFC tag on identification badges 50) associated with, carried by, worn by, or otherwise associated with the respective person. The information is encoded according to the storage medium technology, and may be encrypted. Preferably, each storage medium has a unique identification number (UIN). Additionally, or alternatively, the employee information, patient information, and ancillary person information may be stored and accessed on and from an on-site or remote server. Information is communicated from a person to a waypoint 80 associated with the patient's room to log person check-in and check-out times to and from the room, respectively. The communication may be physical, such as a card swipe of a badge 50, PIN number entry, or biometric scan. Additionally or alternatively, the communication may be remote, such as by use of wireless communication technologies. The communication may be manual (e.g., requiring a person to interact with a waypoint 80) or automatic (e.g., waypoints 80 positioned so as to sense entry/exit of persons to/from a room).

Whereby the employee information, patient information, and ancillary person information is preferably delivered to the display 12 through a computer application, mobile application, or web-based application.

The system 10 also preferably provides a record of care (or work history more broadly) allowing an administrator or other supervisor to view the location at which an employee has been working over a given amount of time and with which customers, patients, or other employees, thereby increasing accountability for the staff and assurance of care for the patient.

The system 10 may also be configured to integrate employee and patient information with an EMR system and/or retrieve employee and patient information from an EMR system.

Additionally, or alternatively, the system 10 tracks and records "critical steps" in the provision of care. Critical steps are steps that are so essential to the provision of care that they require a primary care giver (e.g., senior surgeon or anesthesiologist) to be physically present during the provision of that step of care. Employee accountability may be evaluated with respect to the provision of critical steps and whether certain employees were physically present during the provision of care that involved critical steps.

The system 10 also preferably provides a graphic user interface (GUI) 60 provided on the display 12 with selectable options (e.g., with a computer mouse, touchscreen, keyboard, or other input device) for viewing such as "room view" (FIG. 3), by selecting the room view button 62; "team view" (FIG. 4), by selecting the team view button 64; and "timeline" (FIG. 5), by selecting the timeline button 66, for viewing employee information, patient information, and ancillary person information.

The "room view" preferably displays an image on the display 12 of all persons located in (e.g., checked in) a select room, such as a patient's present or prior ward, an MRI room, an operating room, a counseling room, a chapel, an examination room, etc. Depending on the occupants of the room, employee information, patient information, and/or ancillary person (e.g., guest or family member) information is also preferably included on the display 12. A relationship of the room occupants to a treatment team may be indicated.

The "team view" displays an image of all the various employees and other persons associated with the treatment team providing care for a specific patient. Guests, family members, and/or other categories of individuals may be provided. Employee information is also preferably included on the display 12. In the views, certain care management individuals may be highlighted, such as by being placed in a prioritized location on the display 12, as shown in the views including photographic identifiers below the title "CARE TEAM" and above the remaining team members. The views may also convey information related to team member substitutions (e.g., staffing adjustments, including triage, shift changes, schedule changes, and availability coverage). Team member substitutions may be conveyed on the display by highlighting the assigned, responsible team member and by deemphasizing the replaced team member, such as by defocusing the replaced team member photographic representation or rendering such image in a monochromatic fashion (e.g., graying out the photo). In this way, the most up-to-date information that has been entered into the system 10 may be conveyed to the user.

The "timeline view" displays a timeline of past, present, and/or expected treatment events in chronological order and may include information about the events including employees present and duration of the event. Preferably, the "timeline view" may be selectively organized by events performed for a patient, events performed by a specific employee or team of employees, and/or event type. Preferably, a user may select a certain event and/or employee and the display 12 provides additional information about the employee, for example, employee information.

Preferably, the room view, the team view, and the timeline view are configured to interface with each other, and indeed may be simultaneously displayed completely or partially. For example, from the room view (FIG. 3), a user can select an employee that has been identified in the room with the patient and is then able to view the employee's position within the treatment team in the team view. Additionally or alternatively, interaction times with such employee can be provided. Another example is allowing a user to select a care event from the timeline view (FIG. 5) and having the ability to select an employee from the timeline view to see how the employee fits within a certain treatment team in the team view or whether that employee is currently in the room in the room view.

The user interface allows access to all three types of information (identification of persons in a patient room, a person's role in a treatment team (and a selectable hyperlink, the selection of which will display a definition or explanation of a defined role) or as a guest, and a treatment timeline), or other types of information from within a particular view, thus more efficiently communicating with a patient. For instance, from within a room view, a team view image may be accessed and/or simultaneously displayed. Thus, the system may allow a user to see which of the persons within a user's room are members of the user's team, guests or otherwise categorized. Likewise, from within a room view, a timeline view may be accessed and/or simultaneously displayed. Thus, a user may select from those individuals who are present in a user's room and to see only those individuals who were present in the user's room over a period of time in the past or who are scheduled to appear in the future. From within a team view, a room view image may be accessed and/or simultaneously displayed. Thus, a user may see which members of a given team are within a room (or other area) at a point in time. Likewise, from within a team view, a timeline view may be accessed and/or simultaneously displayed. Accordingly, a user may see which members of a given team are present in a room at the present time, which have been present at a time period in the past or which members are projected to appear at a time in the future or over a future period of time (e.g., highlighting, outlining, or otherwise indicating which members of a team are, have been, or will be within a room, or caring for a patient, from within a team view perspective). From within a timeline view, a room view image may be accessed and/or simultaneously displayed. Thus, a user may select all or some of the employees who are present in a given room and to view (in a timeline view) all of the instances in the past (or in the future, prospectively) when those team members have appeared in the past (or are scheduled to appear in the future). Additionally or alternatively, the system enables a user to use a timeline view that shows a user which members appearing on a timeline are currently present in the user's room (e.g., highlighting, outlining or otherwise designating that an employee who appears on a timeline view is currently present in the user's room or in a given area). A user may select a given member of the user's team (guest or otherwise categorized individual) from room view, team view or timeline view and see only those times on a timeline when the selected member of the team (guest etc.) appeared on a timeline view that shows only those instances when the selected individual has appeared in a given area or in the service of the user. Likewise, from within a timeline view, a team view may be accessed and/or simultaneously displayed. Accordingly, a user may view a timeline view and see which of the individuals who have appeared in a given area over a period of time are members of the user's team, guests or otherwise categorized individuals (e.g., a user could look at a timeline and view only guests who have visited the user to help the user remember who came to visit and when). A selective timeline view may be provided to allow a user to select a given member of the user's team (e.g., from a team view perspective, timeline view perspective or room view perspective) and to choose to view every time that a given team member has appeared in the past (or is scheduled to appear in the future).

Figure 6:
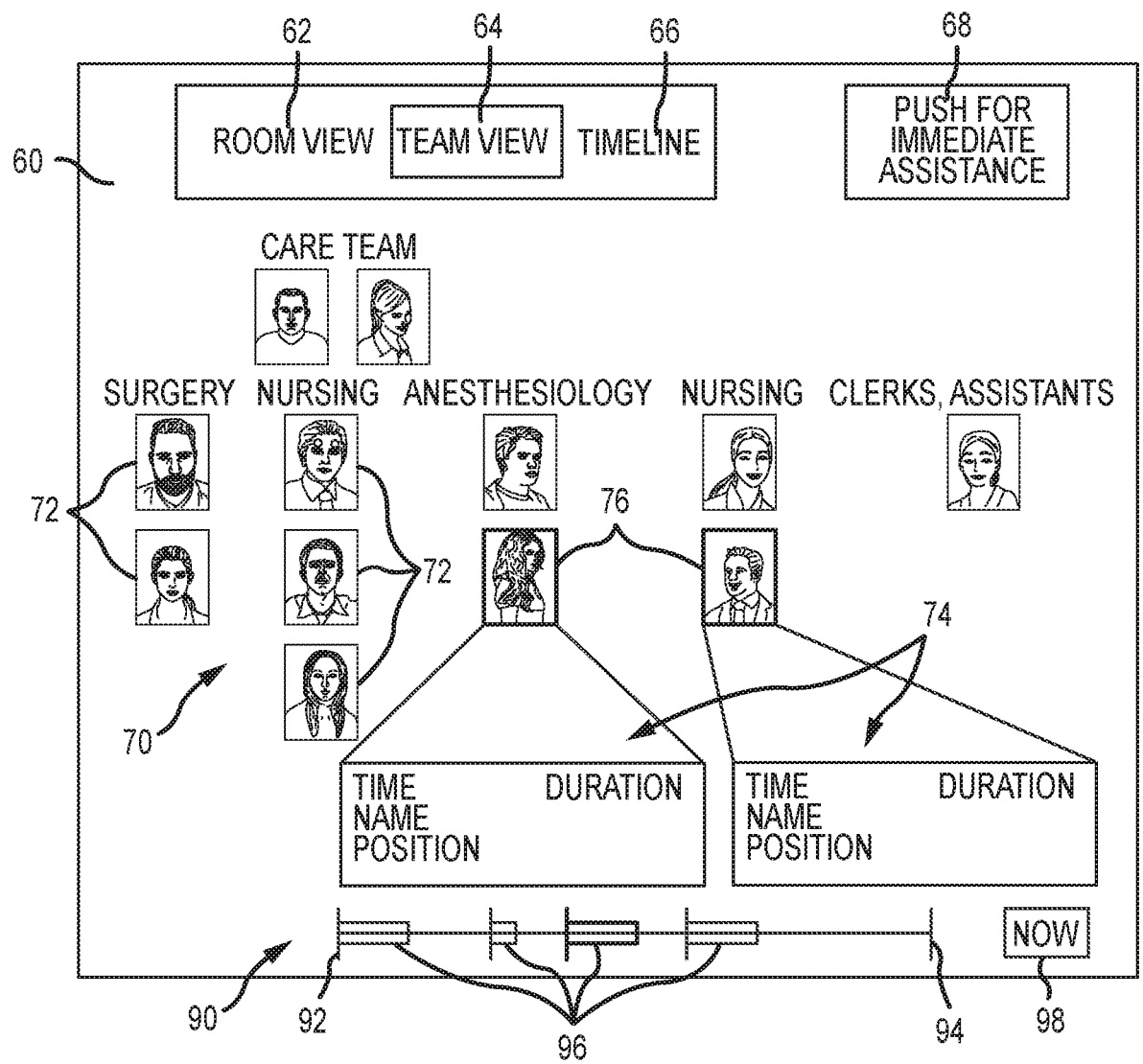
FIG. 6 is a fourth display view according to the present invention.

An example is shown in FIG. 6. On the display 60, there are menu selection items, such as room view 62, team view 64, and timeline view 66, previously described, and a call menu item 68, further described below. While views can be changed, a preferred embodiment of an informational display 60 includes a team display 70 and a timeline display 90. The team display 70 preferably includes a photographic representation 72 of each employee that is expected to be involved in any portion of a treatment regimen, a portion or an entirety of which is displayed along the timeline display 90. A user selection of one or more of the photographic representations 72 results in a display of team member information 74 and preferably a highlight 76 of the selected team members. The team member information 74 may include the employee's name and/or title or position. Team member information 74 may further include time indicators, such as an indication of the most recent previous time(s) and/or date(s) that the employee was checked into and/or out of the patient's room. Additionally or alternatively, a time indicator may provide an indication of the next time(s) and/or date(s) that the employee is expected to check into and/or out of the patient's room. Additionally or alternatively, a time indicator may provide an indication of past and/or future durations of time during which the employee was checked into the patient's room. The highlight 76 may be provided on the display 60 by one or more of bolding a photographic border (as shown), enlarging the selected team member photos, tiling the selected team member photos, and defocusing unselected team member photos.

The timeline display 90 preferably extends from a start time 92 (e.g., patient intake date/time) to an end time 94 (e.g., patient discharge date/time). Between the start time 92 and end time 94 is preferably one or more treatment regimen stages 96. A user selection on the timeline display 90 preferably effects a selection of one or more of the photographic representations 72, and display of team member information 74, as described above. Thus, a user is preferably capable of selecting any portion or stage 96 of a treatment regimen to highlight or otherwise identify team members that are or were or will be involved with, or are or were scheduled to be involved with, the selected stage 96. If a user would like to highlight and identify team member information 74 related to team members that have been checked into or otherwise recognized as being presently in the patient's room, a NOW button 98 may be selected. Selection of the NOW button 98 effects a selection of the timeline stage 96 encompassing the present date and time, if any, which in turn effects a selection of one or more of the photographic representations 72, if any are presently associated with the patient's room, and display of team member information 74, as described above. In this way, the provision of services, such as medical services, to the patient or other user is made more efficient by eliminating a necessity of initial or repeated personal introductions of treatment team members. Contemporaneously, a staff service and/or location log may be generated for site use, as further described below.

Preferably, ancillary persons (e.g., guests) may be filtered based on parameters such as their contact information and/or the locations/times at which they have visited a patient.

Figure 3:
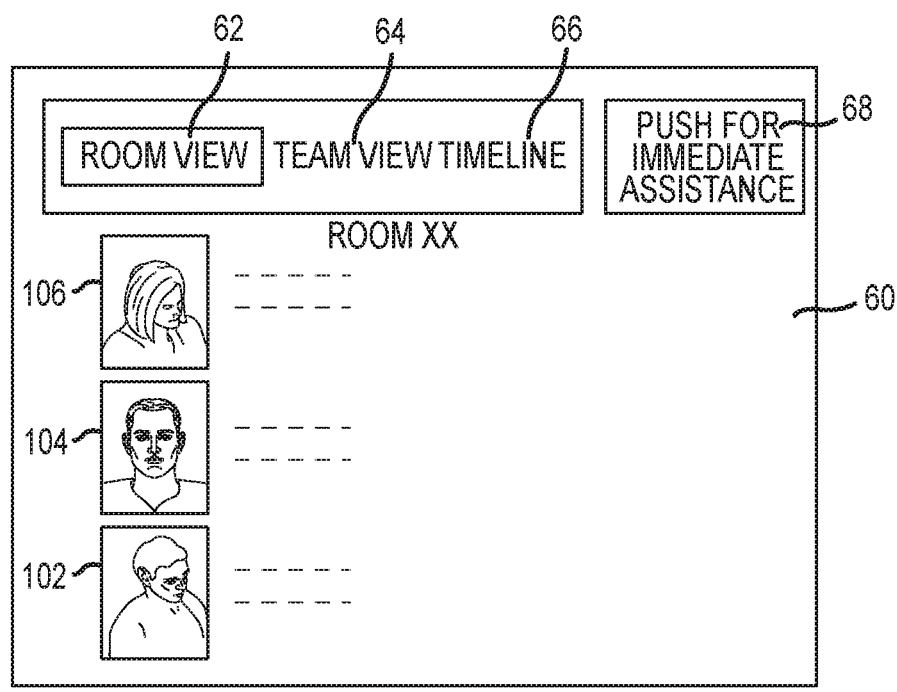
FIG. 3 is a first display view according to the present invention.
Figure 4:
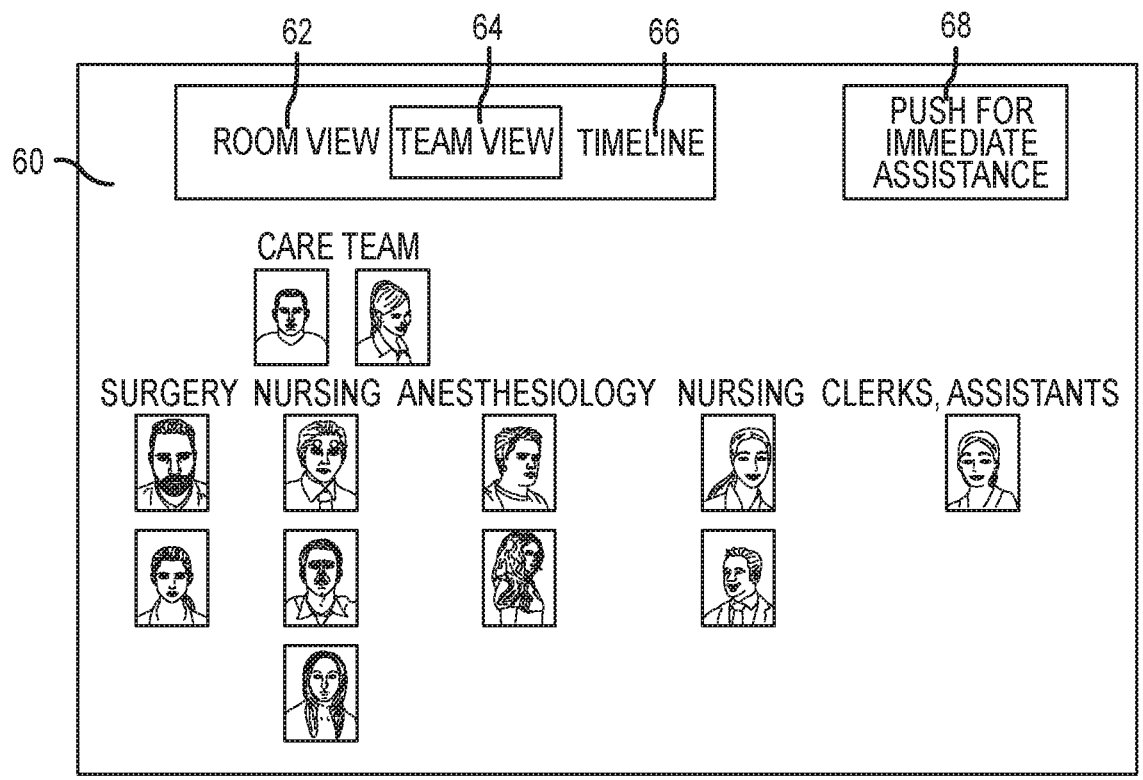
FIG. 4 is a second display view according to the present invention.
Figure 5:
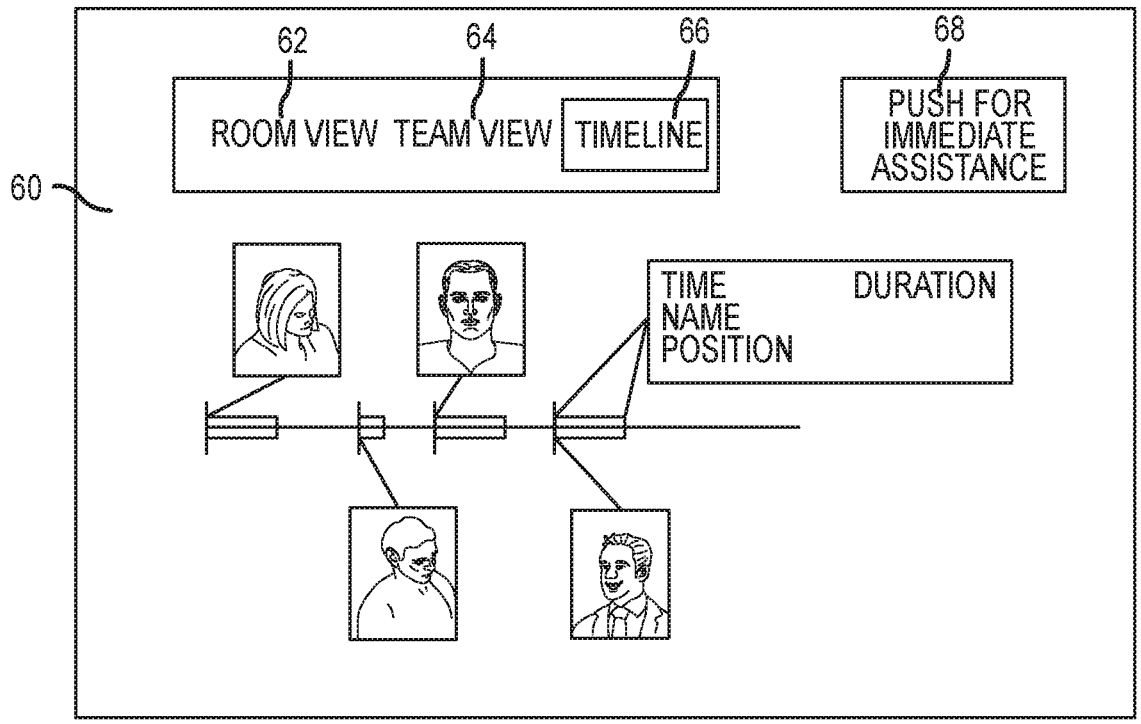
FIG. 5 is a third display view according to the present invention.

The system 10 also preferably provides a user with the option on the GUI of requesting assistance, as depicted in FIGS. 3-5 with an immediate assistance button 68 labeled, "Push For Immediate Assistance." Preferably, once the immediate assistance button 68 is selected by the user, the system routes the user request to the employees or a select employee on the treatment team. The system 10 will preferably log the request and the time at which it was placed. The system 10 will also preferably start a forward delay timer at the time of the request to track the time it takes for an employee to respond to the request by the user. The system 10 may also communicate a reminder to a predetermined employee and/or additional predetermined employees (e.g., up a predetermined chain of command or authority) after a predetermined time elapses on the forward delay timer, such communication being in a role-lateral and/or role-hierarchy method (forwarding the assistance request to to attempt to ensure that the assistance request is attended to. After assistance has been rendered the act may be recorded as complete by a user (i.e., at least one of the patient or the employee) and the record may be shown on the timeline provided in the "timeline view" (FIG. 5). Options for requesting assistance may include categorization, such as facilities (e.g., bedding, pillows), nourishment (e.g., food/water), medication, and/or physical assistance (e.g., help with getting dressed or ambulation). Assistance requests may also be freely inputted by a user (such as with a physical or virtual keyboard), in which case the request may be manually or automatically routed to appropriate care provider(s).

The system 10 preferably comprises a mechanism for preventing record fabrication such as, but not limited to, a voice recognition or other biometric recognition step.

Other contemplated features include providing a map feature which would help guide a user to a certain room, guest service, facility, or person; an alert to notify the user and/or an employee if a non-employee user enters an unauthorized area; an alert to notify the user and/or an employee that a non-employee user has left a certain room or area; and having designated way-points 80 (FIG. 2) located throughout a healthcare facility 100 which detect the presence of employees, patients, and ancillary persons and can interface with the server of the system to log the location, time, and duration of the detection of that person. Notifications may be provided through audible sounds and/or tactile feedback such as through vibration.

The system 10 also preferably is configured to create and store user logs (uLogs), employee logs (eLogs), visitor or guest logs (i.e., ancillary persons) (vLogs), and/or waypoint logs (wLogs) of care giving and visitation events and other information such as detecting, or accepting input from, employees and ancillary persons that pass by waypoints 80. Preferably, the system 10 is configured to compile and allow viewing of the uLogs, eLogs, and vLogs. The various logs may be used by the facility (e.g. hospital) for process improvement, accounting, employee performance reviews, auditing, etc.

Regarding hardware implementation, each display 12 is driven by an associated display driver (not shown), which may be local to a patient's room, located remotely yet within the same facility (e.g., a hospital) as the room, or located remotely from the facility, such as over a wide area network (WAN) or the internet. The waypoint(s) 80 is/are preferably in communication with electronic memory to enable updating of present team member information and related schedules.

Figure 7A:
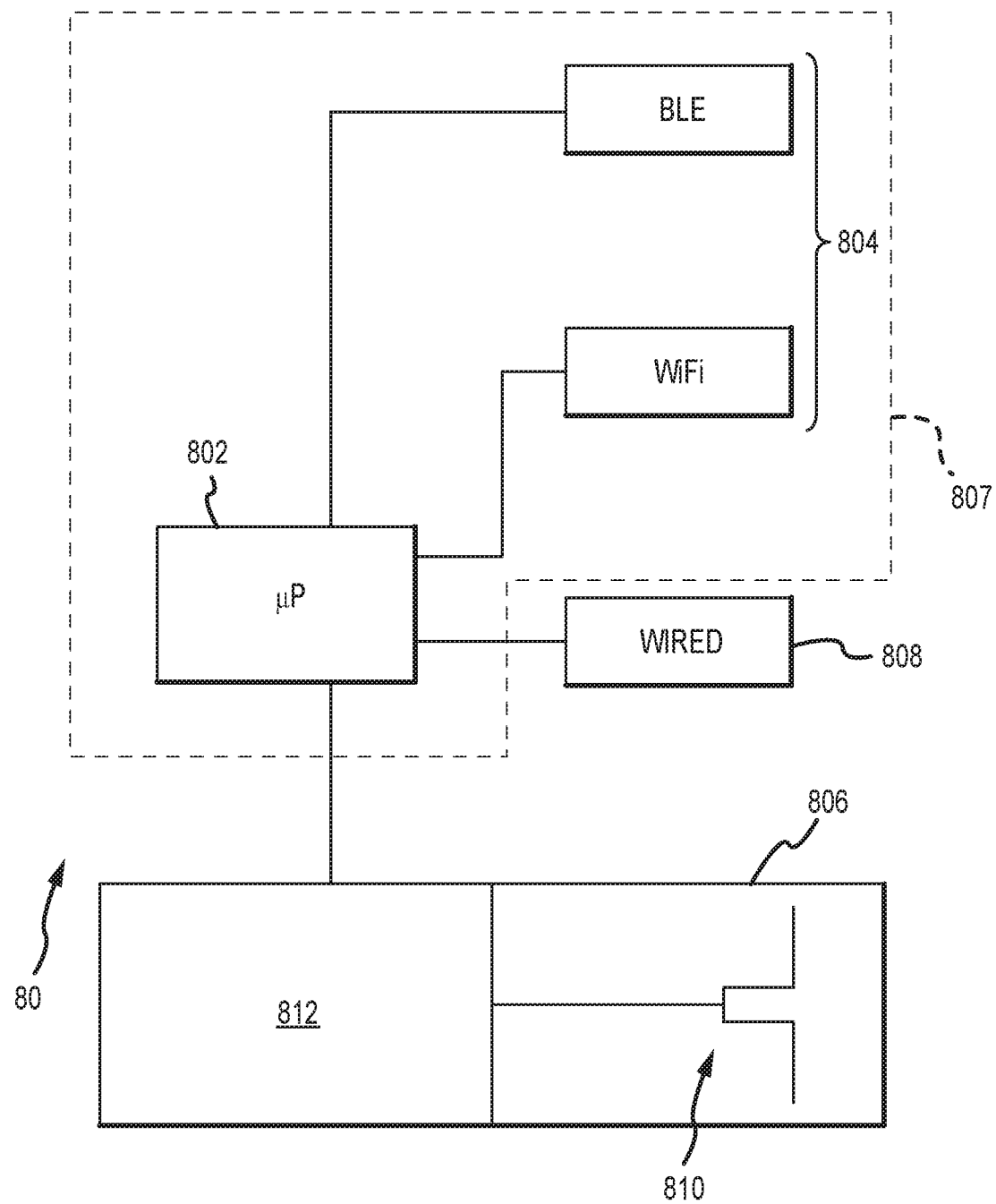
FIG. 7A is a block diagram schematic view of a first waypoint according to the present invention.
Figure 7B:
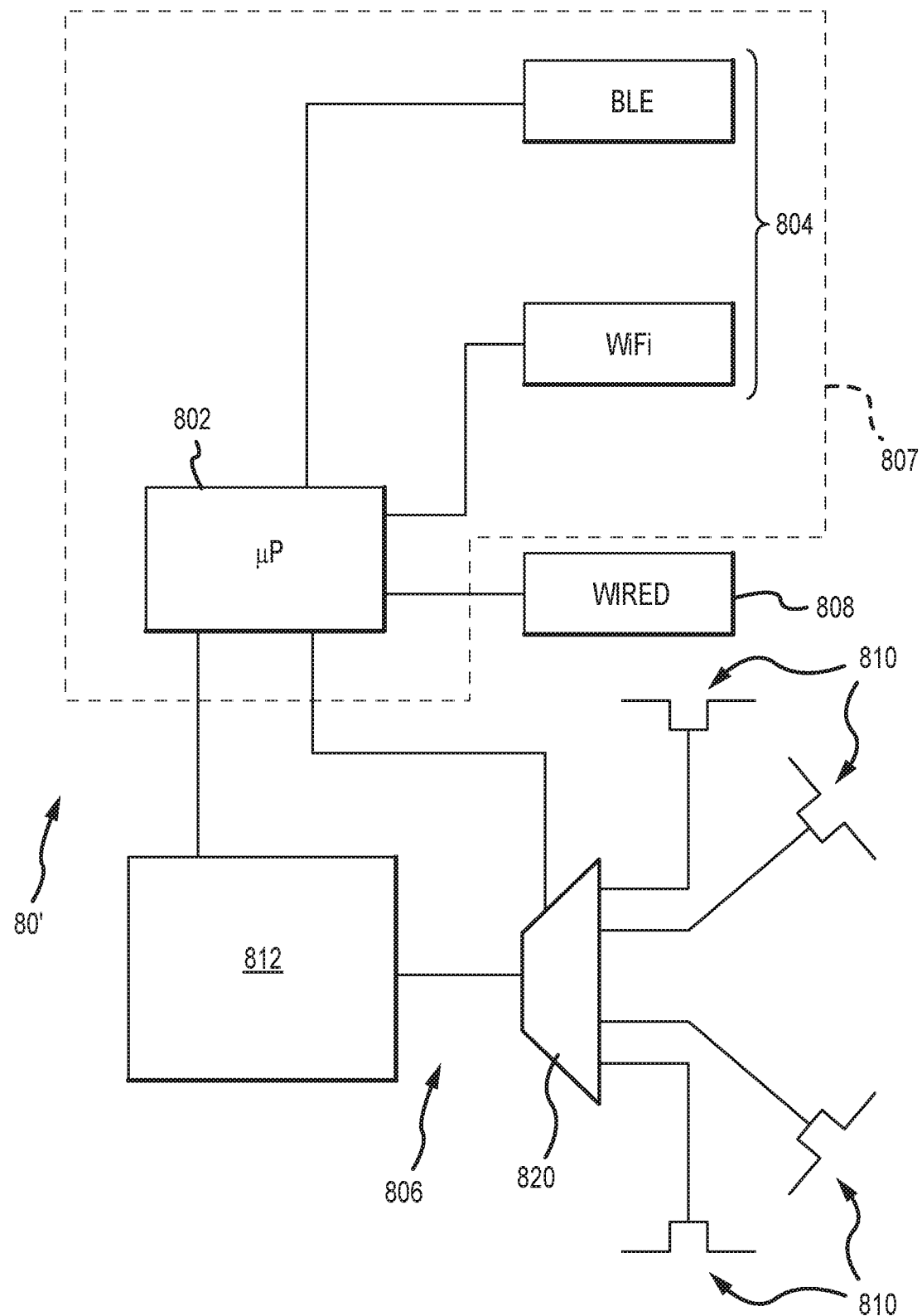
FIG. 7B is a block diagram schematic view of a second waypoint according to the present invention.

Generally, with reference also to FIGS. 7A and 7B, a waypoint 80 includes one or more microprocessors 802 in operative electrical communication with one or more wireless communication interfaces 804 (e.g., Bluetooth, WiFi (IEEE 802.11)), and one or more wireless code detection interfaces 806 (e.g., ultra high frequency (UHF) radiofrequency identification (RFID) interface). The microprocessor 802, Bluetooth® and WiFi interfaces 804 may all be provided in a system-on-a-chip (SoC) format, such that they are all contained within a single electrical component package 807 to be mounted on a printed circuit board (PCB). Additionally or alternatively, wired communications connections 808 may be provided, such as RS485/422 or Ethernet connections, using known hardware connection interfaces. A preferred wireless code detection interface 806 includes a passive-backscatter, interrogator-talks-first, RFID system in the UHF range, including an antenna 810 communicatively coupled to an RFID detector module 812. A preferred antenna 810 is a linear polarized dipole antenna. An alternative antenna 810 may be a circular or elliptical polarized patch or panel antenna. FIG. 7B provides an alternative block diagram schematic of a waypoint 80' that includes multiple antennae 810 connected to an antenna switch 820, which is controlled by the microprocessor 802. Accordingly, the multiple antennae 810 may be positioned to detect RFID tags in various locations throughout a physical space (such as a doorway or room or portion of a room) and the microprocessor 802 can switch between the various antennae 810 (which are preferably connected to the switch via coax cable) at a predetermined or variable rate. A preferred antenna switch 820 is capable of a switching rate of about 25 kHz and supports RF frequencies of 300 MHz to about 1 GHz.

The wireless code detection interface 806 is capable of detecting codes within a particular direction and range of the antenna 810. Generally speaking, RFID systems are known to detect RFID tags (e.g., single or dual dipole, dry or wet inlay) in a manner described, for example, in U.S. Pat. No. 7,417,548, which is incorporated herein by reference in its entirety.

Figure 8:
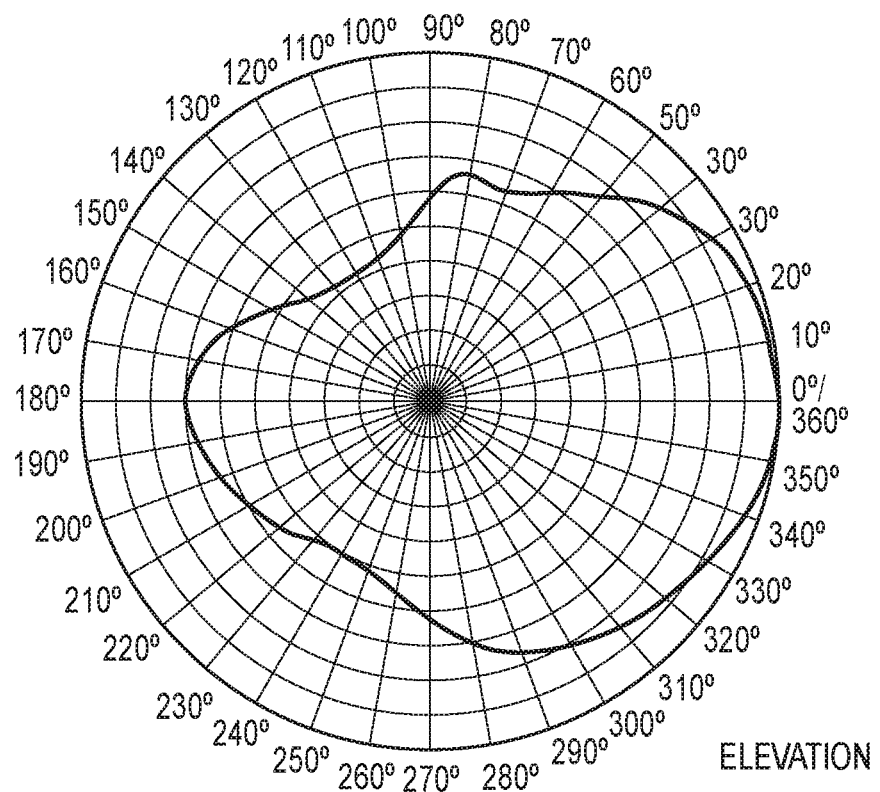
FIG. 8 provides graphical representations including exemplary dipole antenna field elevation and azimuth radiation patterns.
Figure 8:
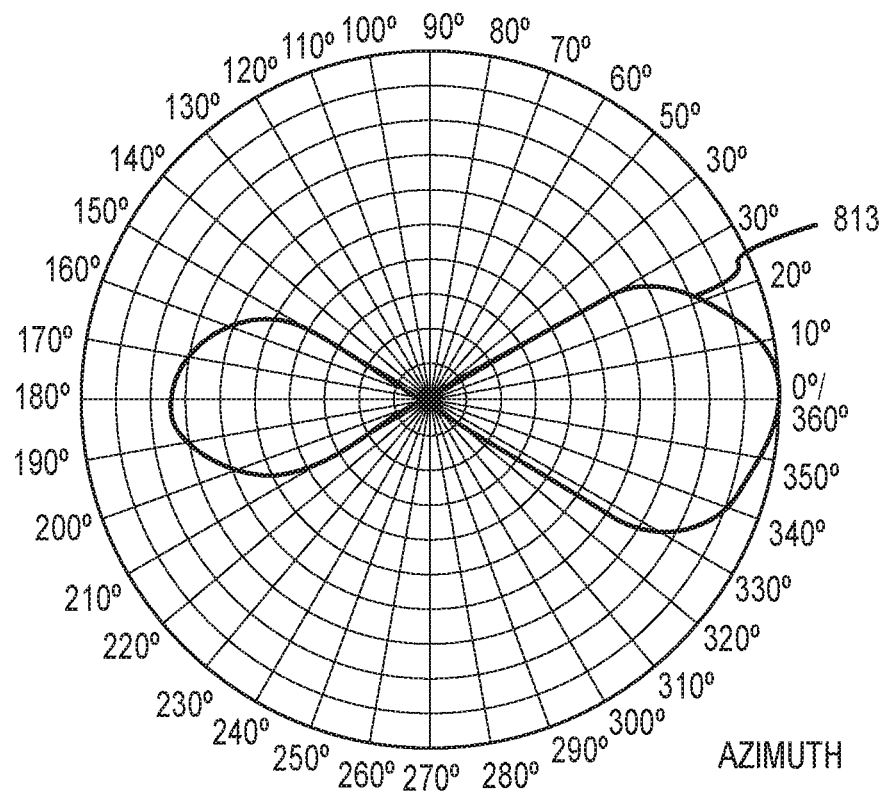
Figure 9A:
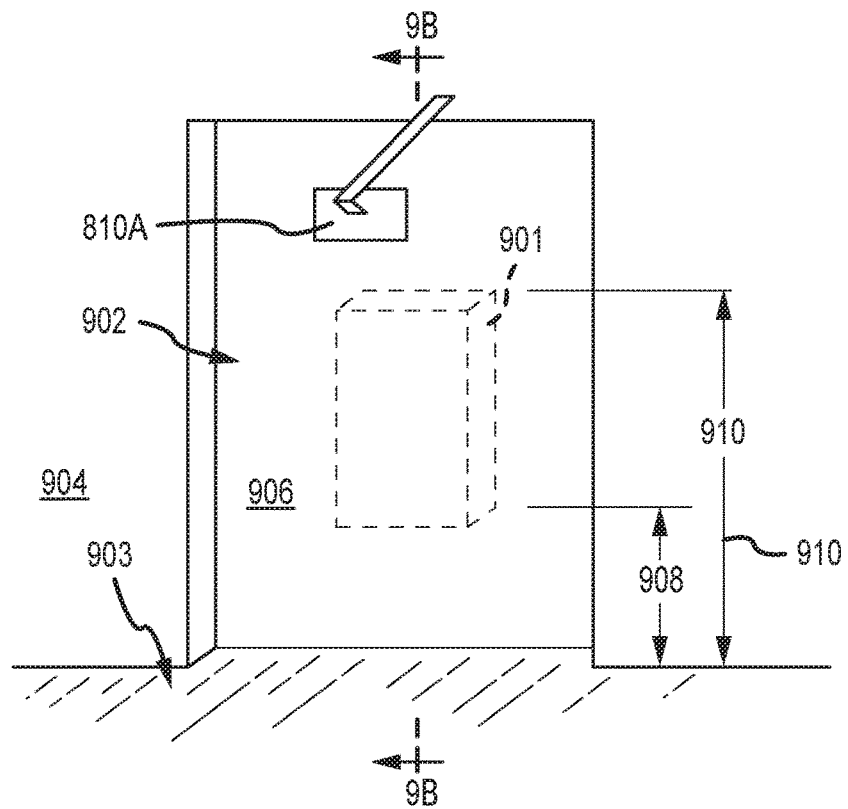
FIG. 9A is a perspective view of a physical space according to the present invention.
Figure 9B:
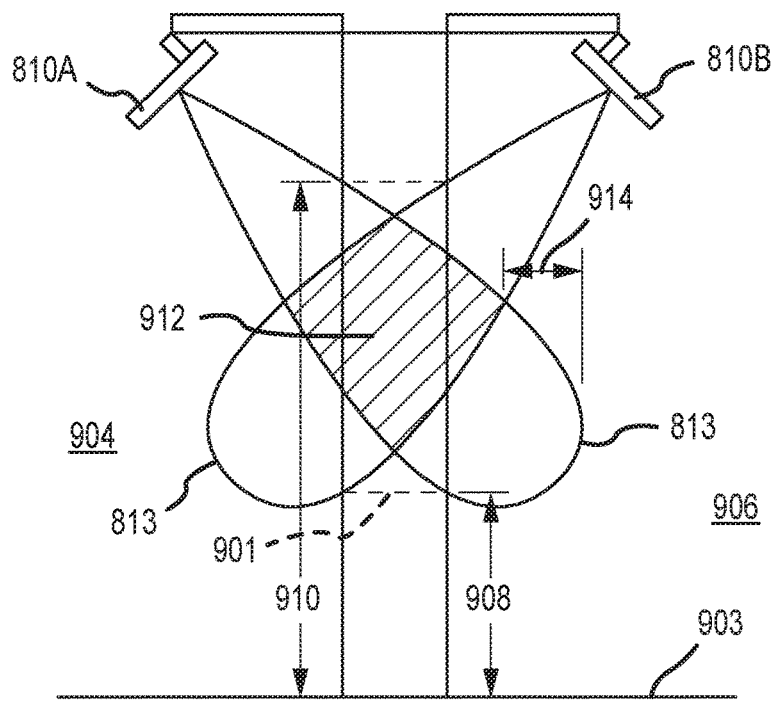
FIG. 9B is a cross-section taken along line 9B-9B of FIG. 9A.

While a waypoint 80 may be installed as previously described, a preferred one or more waypoints 80 are arranged to automatically detect RFID tags within a given space. Antennae have measurable radiation patterns, including field elevation and azimuth patterns. An example of such field patterns is shown in FIG. 8 for a linearly polarized antenna. Generally, however, most antennae (even most circular polarized antennae) will have asymmetric radiation patterns including a main lobe 813, which may take on various shapes. FIGS. 9A and 9B help to illustrate a system and method for detecting codes (e.g., RFID tags) within a given physical space 901. A doorway 902 extends upwards from a floor 903, between a room 904 and another room or hallway 906. Alternatively, the space 901 may be defined within a room, such as a hospital room, which preferably contains one or more patient beds. The space 901 is defined to more advantageously align one or more code readers 810A,B to detect codes (e.g., RFID tags) within the space 901. The space 901 is preferably defined between a lower height 908 and an upper height 910, each measured vertically from the floor 903. A preferred lower height 908 is defined about 50 centimeters to about 80 centimeters from the floor 903. A preferred upper height 910 is defined at about 150 centimeters from the floor 903. As can be seen in FIG. 9B, the radiation patterns from the respective code detectors 810 may be positioned to overlap in a majority of the physical space 901. This overlap 912 may be used to help prevent inaccurate code detection occurring outside of the physical space 901, such as in the other room (or portion of a room) or hallway 906. That is, if code detection information from both code detectors 810A,B is analyzed and compared (e.g., whether a code is detected by both detectors 810A,B or just one), false detections may be lessened, or eliminated, by narrowing a detection field by some horizontal distance 914.

Figure 10:
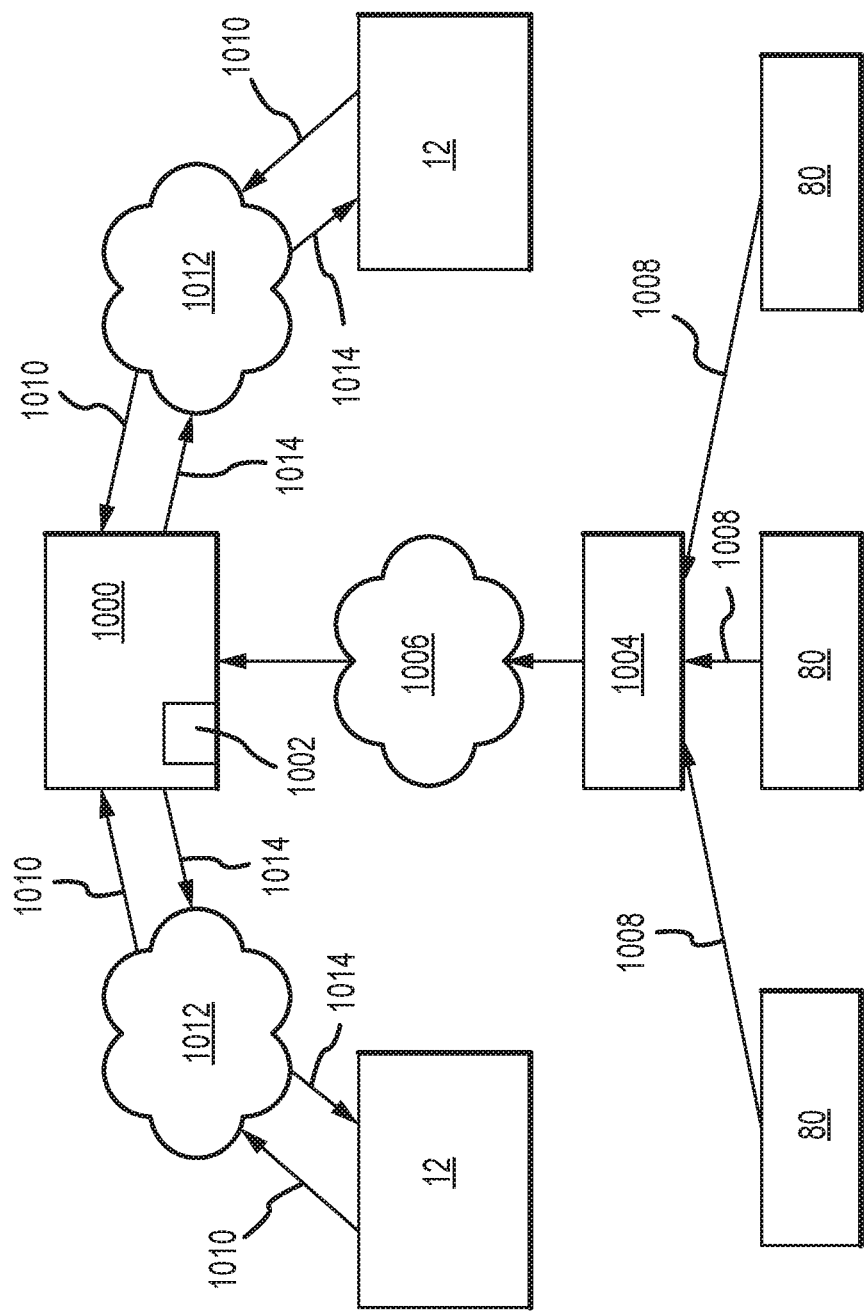
FIG. 10 is a block diagram of communication flow of a system according to the present invention.

FIG. 10 shows a block diagram schematic regarding communication flow among and between elements of a system according to the present invention. A database management system 1000 includes a database 1002, which stores information accessible by the display device 12. The database management system 1000 is communicatively coupled to the waypoints 80 or a waypoint manager or router 1004 over a communication network 1006, which may be a wired and/or a wireless network (e.g., WAN, LAN, internet). Generally, information is sent by waypoints 80 through the router 1004 and the network 1006. Information may be sent using known methods of transmitting information, such as through application programming interfaces (APIs). Examples of functionality allowing a transfer of data are hypertext transfer protocol (HTTP) uniform resource locator (URL) requests that are processed using cloud function technology, including GET requests, POST requests, PATCH requests, etc. Receipt of a request (which preferably contains an internet domain, query and associated paramaters in string format) causes a cloud function (e.g., script) to read what the parameters are from the request. The script may perform a search of the database 1002 to see if certain information has yet been recorded (e.g., if an RFID tag code has been entered and associated with a particular space, such as a hospital room). The cloud function then preferably updates the database to log a code and timestamp (either a time received as a parameter or generated locally or accessible by the script), and associate it with a physical space. The manager also assigns relationships between objects (e.g., patients, staff, and visitors), and such relationships may be hierarchical based on weighting of various characteristics of the objects.

In an HTTP request as used in an exemplary implementation, the URL domain directs communications from an internet enabled device to a server, which may be a cloud-based server. As a part of the HTTP string, the type of request is sent to the respective URL (e.g. GET, POST, PATCH, etc.), as well as possibly a JavaScript Object Notation (JSON) (a specifically formatted string). The JSON or other strings may then be used to send alternative or additional data to the database. In a preferred embodiment, however, the requisite operational data is contained within the URL sent by the waypoints 80 to the database manager 1000. The database (or cloud function), preferably once data is received without loss and no errors executing the code server side, may send a confirmation string back to the respective waypoint 80, reflecting receipt success or requesting other information that may be desired or required (also a string format).

Data recorded in the database 1002 preferably includes instances of code presence (e.g., visits of an object or person through the physical space 901) in the defined physical space 901 or overlap 912. Information related to a code presence (or code detection) can include one or more of a code (e.g., RFID tag identification number), a building identifier, a room identifier, a room partition (e.g. curtained-off area) identifier, a timestamp (e.g., time of day and/or date), and an indicator of entrance and/or exit.

Thus, generally, waypoints 80 include code detectors to detect the presence of a code within a physical space 901. The frequency of attempted code detection by a waypoint 80 is preferably controlled by its associated microprocessor 802 and/or detector 812, and duplicative detections (e.g., extended presence of a code in the space 901) may be discarded or recorded for posterity. Once a code is detected, a waypoint 80 sends information 1008 related to that code detection through a router 1004 and over a network 1006 using a URL, preferably with string data included. The data manager 1000 (which may be distributed amongst cloud-based functions and scripts) receives and parses the URL, data within the database 1002 is updated to reflect the code detections from the waypoints 80.

The information and/or logs are preferably stored in nonvolatile memory in a computing device (e.g. in a database), such as a server, hard drive, solid state drive, etc. The memory is accessed and information is retrieved therefrom through user interaction with a display 12. However, when a user interaction with the display 12 causes a query 1010 of the information, reduced network 1012 traffic may be achieved by limiting the number of network queries 1010. The network to which the display device 12 is communicatively coupled may be the same communication network over which the waypoints 80 communicate with the router 1004 and/or the same communication network 1006 over which the router 1004 communicates with the data manager 1000. Network queries 1010 may be limited by responding 1014 with complete information related to a particular user to allow the data to be stored locally (e.g., downstream from the server) and updated only when needed. Additionally or alternatively, information may be pushed 1014 from the memory to the display 12 proactively. The computing device 1000 may be local to a patient's room, located remotely yet within the same facility (e.g., a hospital) as the room, or located remotely from the facility and accessible over a network, such as a wide area network (WAN) or the internet. Remote guest visitation is contemplated, such that a user authorization (e.g., username and password) may be provided to a user located outside of the facility (e.g., hospital), and located perhaps miles (tens of miles, hundreds of miles, or thousands of miles) away. Remote access to a particular patient's data is preferably controlled in accordance with the law and shared only with permission of the patient, or as necessary for provision of care to the patient, or for facility diagnostics.

Many variables of information storage are possible, and may be stored in the database 1002 in a relational database format or flat table format. A relational database according to an embodiment of the present invention may include tables capable of storing information related to team member departments, team member roles (e.g., titles) and descriptions, room numbers and/or types, treatment regimens (which may include multiple treatment regimen stages), treatment regimen stages (including, e.g., room number or type, duration, and/or description), team member data (name, photo, identification number, schedule, manager), patient data (name, identification photo, patient identification number, insurance carrier, insurance identification number (e.g., group ID, subscriber ID), other person data (e.g., guest name, visitation permissions, duration of visit, online access).

Retrieval of stored information may be highly customizable through administrative/data management access (e.g., system administration), while retrieval of stored information through ordinary user access (e.g., patient/guest access) may be limited in a number of ways. One way in which information retrieval through user access may be limited is by formulating predetermined information queries, and providing a limited number of options for a user to select information viewing.

Access to the information may be governed by a username and password or PIN number combination, so as to ensure accuracy in the information displayed to a particular user.

The foregoing is illustrative only of the principles of embodiments according to the present invention. Modifications and changes will readily occur to those skilled in the art, so it is not desired to limit the invention to the exact disclosure herein provided. While the preferred embodiment has been described, the details may be changed without departing from the invention.

What is claimed is:

1. A system comprising:
    a first code detector capable of detecting a first code and a second code in a physical space in a healthcare setting, the first code detector being communicatively coupled to a communication network and capable of transmitting code detections over the network;
    a data manager capable of monitoring and analyzing the code detections sent by the code detector over the communication network;
    an informational database capable of storing code detection information from and providing code detection information to the data manager; and
    a display device located in a physical space, also including a patient, the display device receiving code detection information from the data manager, the display device comprising a timeline view that graphically displays a time differential that occurs between a first time at which the first code is detected in the physical space and a second time at which the first code is detected in the physical space.

2. The system according to claim 1, wherein the first code is logically associated with a representation of the patient in the informational database, and the first code is physically associated with the patient.

3. The system according to claim 1, wherein the second code is logically associated with a representation of a first healthcare provider in the informational database, and the second code is physically associated with the first healthcare provider.

4. The system according to claim 1, the communication network comprising a wireless communications network.

5. The system according to claim 1, the code detections comprising information sent to a uniform resource locator (URL) over the communication network.

6. The system according to claim 5, the data manager comprising a software script hosted at the uniform resource locator, the script being executed as a result of receipt of one of the code detections, the script providing at least a portion of the capability of monitoring and analyzing the code detections sent by the code detector over the communication network.

7. The system according to claim 1, wherein the physical space comprises a doorway.

8. The system according to claim 1, further comprising a second code detector capable of detecting the first code and the second code in the physical space, the second code detector being communicatively coupled to the communication network and capable of transmitting code detections over the network.

9. The system according to claim 8, wherein each code detector comprises at least one antenna.

10. The system according to claim 9, wherein each antenna has a radiation pattern, and all antenna radiation patterns overlap throughout a majority of the physical space.

11. The system according to claim 1, wherein each code detection comprises information indicating at least one of the first code, the second code, the physical space, a building containing the physical space, and time of day.

12. The system according to claim 1, wherein the physical space comprises 5 less than an entire room in the building, the room containing at least one bed.

13. The system according to claim 12, wherein the building is a hospital.

14. The system according to claim 1, the display device further comprising a room view that graphically displays information associated with the second code, the graphical display being accessible between the first time at which the second code is detected in the physical space and a second time at which the second code is detected in the physical space.

15. The system according to claim 1, wherein the first code detector is capable of detecting a third code in the physical space, the third code physically and logically associated with a second healthcare provider and the display device further comprising a team view that graphically displays information associated with the second code and information associated with the third code, the graphical display presenting the second code information related to the third code information in a hierarchical fashion.

16. A method comprising the steps of:
    Automatically detecting a first entry of a first code in a physical space in a healthcare setting, the physical space also including a patient;
    transmitting a first set of parameters to an automated database manager;
    after detecting the first entry of the first code, detecting a first entry of a second code in the physical space;
    transmitting a second set of parameters to the automated database manager;
    after detecting the first entry of the second code, detecting a second entry of the second code in the physical space; and
    transmitting a third set of parameters to the automated database manager,
    wherein each set of parameters include at least two of the following: information related to a building housing the physical space, information related to the physical space, code information, and a timestamp, and
    wherein the sets of parameters affect an informational display in the physical space.

17. The method according to claim 16, wherein, prior to detecting the first entry, the first code had been physically associated with the patient and the second code had been physically associated with a healthcare provider.

18. The method according to claim 16, wherein the physical space includes at least a portion of a doorway defined above a floor.

19. The method according to claim 18, wherein the physical space extends from a height of about 50 cm from the floor to a height of about 150 cm.

20. The method according to claim 19, wherein the physical space extends from a height of about 85 cm to a height of about 150 cm.

21. The method according to claim 16, wherein the physical space includes a portion of a room, the room including at least two beds.

22. A method comprising the steps of:
receiving from a code detector a first set of parameters relating to a first code associated with a patient located in a physical space;
after receiving the first set of parameters, receiving from the code detector a second set of parameters relating to a second code associated with a healthcare provider;
after receiving the second set of parameters, receiving from the code detector a third set of parameters relating to the second code; and
after receiving the third set of parameters, responding to a request from a display device located in the physical space, such responding comprising transmitting to the display device information logically associated with the second code in an informational database and a time differential determined by a difference in time between a respective timestamp received in each of the second and third sets of parameters.

23. The method according to claim 22, wherein the information includes at least one of a photograph of the healthcare provider and employee information of the healthcare provider.

\* \* \* \* \*